United States Patent
Wanca

(10) Patent No.: US 9,067,044 B2
(45) Date of Patent: Jun. 30, 2015

(54) METHOD, SYSTEM AND APPARATUS FOR INTEGRATED DYNAMIC NEURAL STIMULATION

(71) Applicant: Frank M. Wanca, Kihei, HI (US)

(72) Inventor: Frank M. Wanca, Kihei, HI (US)

(*) Notice: Subject to any disclaimer, the term of this patent is extended or adjusted under 35 U.S.C. 154(b) by 255 days.

(21) Appl. No.: 13/766,560

(22) Filed: Feb. 13, 2013

(65) Prior Publication Data

US 2013/0216055 A1    Aug. 22, 2013

Related U.S. Application Data

(60) Provisional application No. 61/600,354, filed on Feb. 17, 2012.

(51) Int. Cl.
| | |
|---|---|
| A61M 21/02 | (2006.01) |
| H03G 5/00 | (2006.01) |
| H03G 9/00 | (2006.01) |
| A61M 21/00 | (2006.01) |

(52) U.S. Cl.
CPC .............. *A61M 21/02* (2013.01); *H03G 5/00* (2013.01); *A61M 2021/0027* (2013.01); *A61M 2205/3375* (2013.01); *A61M 2205/502* (2013.01); *H03G 5/005* (2013.01); *H03G 9/005* (2013.01)

(58) Field of Classification Search
None
See application file for complete search history.

(56) References Cited

U.S. PATENT DOCUMENTS

| | | | |
|---|---|---|---|
| 5,347,083 A * | 9/1994 | Suzuki et al. | 84/613 |
| 8,290,174 B1 * | 10/2012 | Simon | 381/82 |
| 2003/0121401 A1 * | 7/2003 | Ito | 84/625 |
| 2003/0200859 A1 | 10/2003 | Futamase et al. | |
| 2008/0188268 A1 | 8/2008 | Kim et al. | |
| 2009/0079833 A1 | 3/2009 | Abraham et al. | |
| 2009/0180652 A1 | 7/2009 | Davis et al. | |
| 2010/0042024 A1 | 2/2010 | Winkler | |
| 2010/0121411 A1 | 5/2010 | Hochmair et al. | |
| 2010/0198375 A1 | 8/2010 | Rottler et al. | |
| 2010/0210896 A1 | 8/2010 | Davis | |
| 2010/0306744 A1 | 12/2010 | Bates et al. | |
| 2012/0031256 A1 * | 2/2012 | Tsuchiya et al. | 84/604 |

OTHER PUBLICATIONS

Written Opinion and International Search Report dated May 30, 2013, as issued in corresponding International Application No. PCT/US2013/025955, filed Feb. 13, 2013, 13 pages.
Tinnitus Help—ITunes.apple.com/us/app/tinnitus-help/id382593362?mt=8, Mar. 29, 2012.

* cited by examiner

*Primary Examiner* — Paul Huber
(74) *Attorney, Agent, or Firm* — Maier & Maier, PLLC

(57) ABSTRACT

A method for integrated dynamic neural stimulation. The method can include selecting a tone for playback, adjusting the characteristics of the tone, selecting program options for modifying the playback of the tone, selecting an accompaniment to the tone, generating an audio program by combining the tone and the accompaniment according to the selected program options, and playing the audio program via an audio output device having at least a right channel and a left channel.

20 Claims, 9 Drawing Sheets

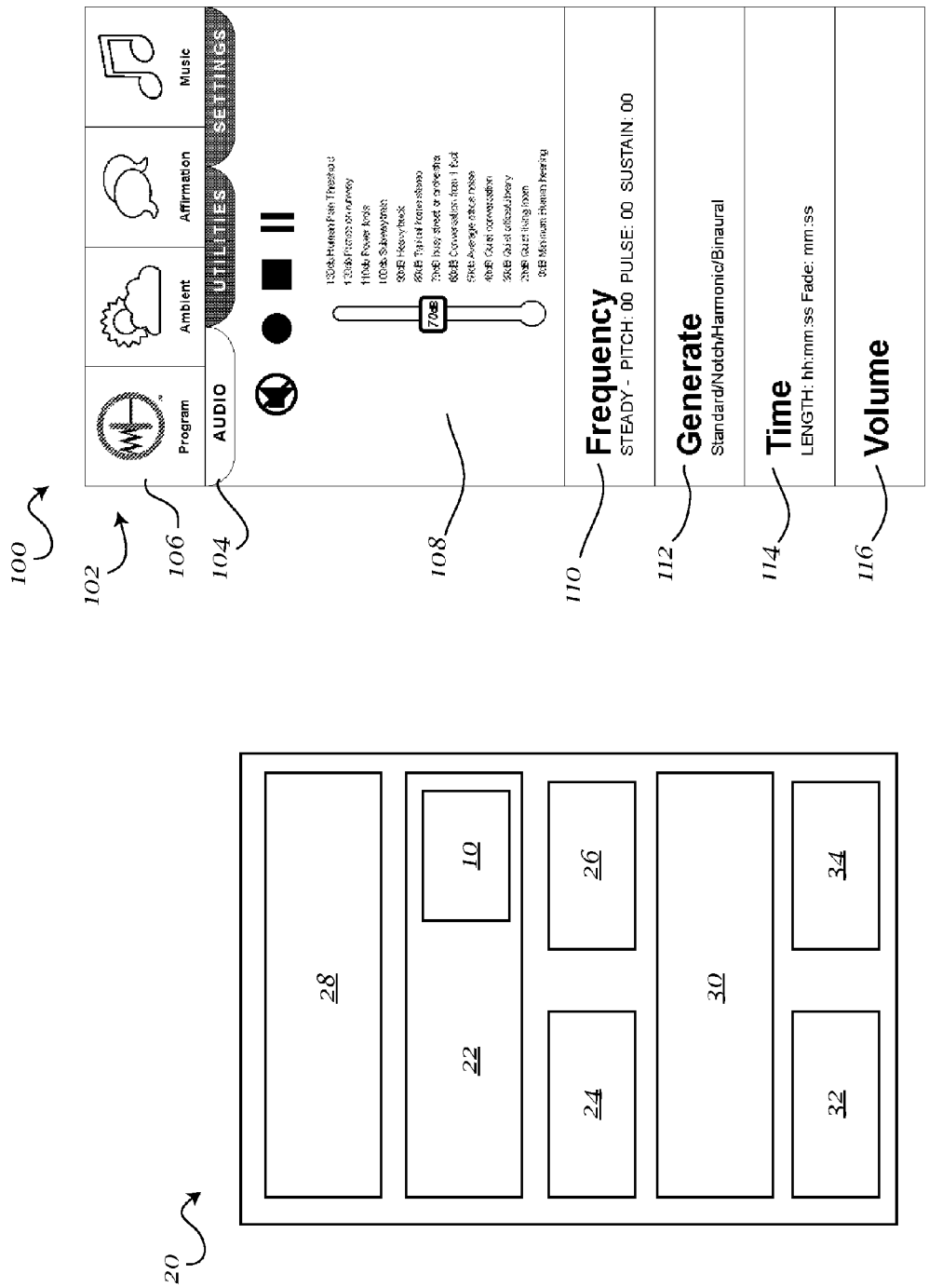

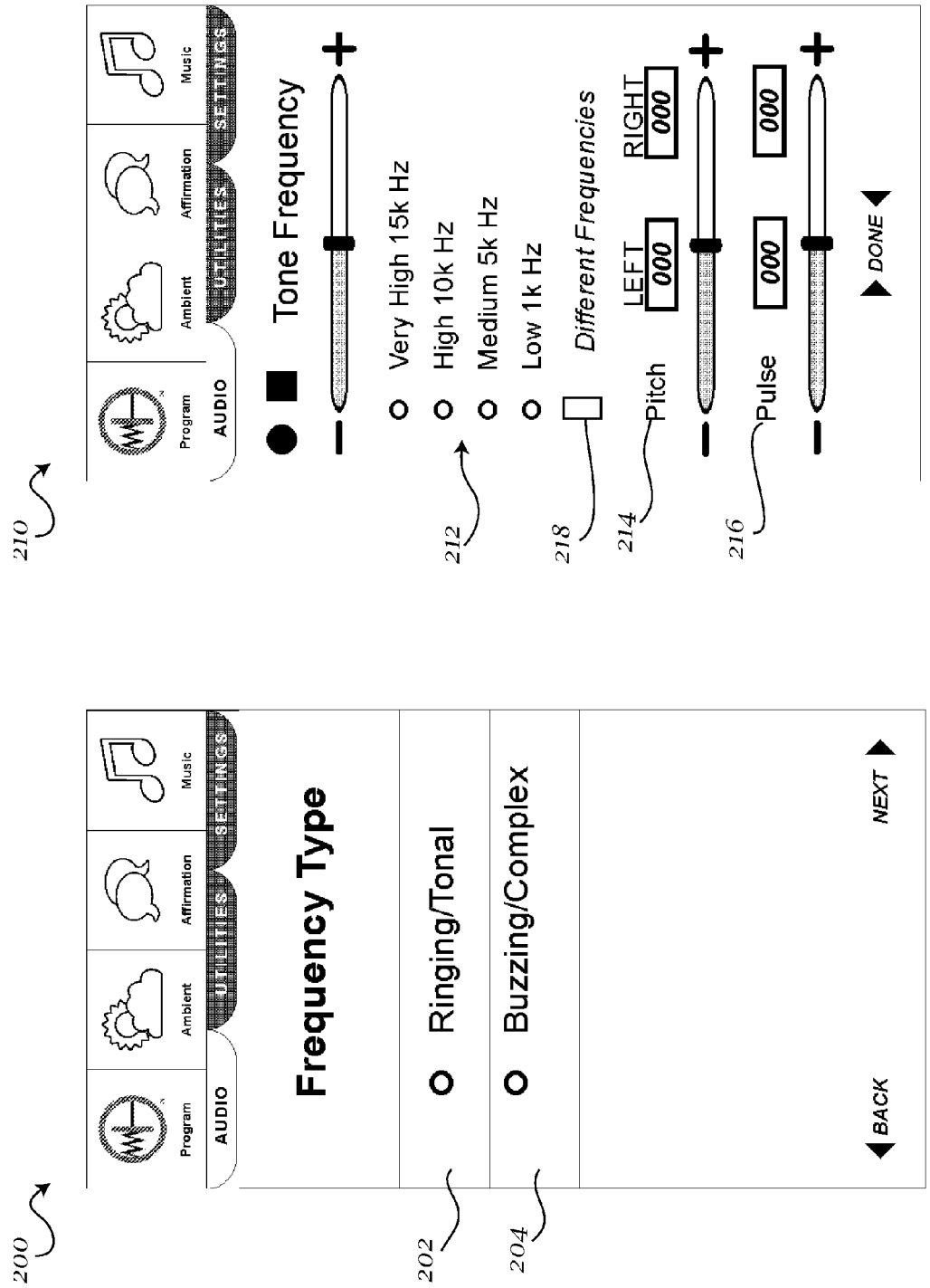

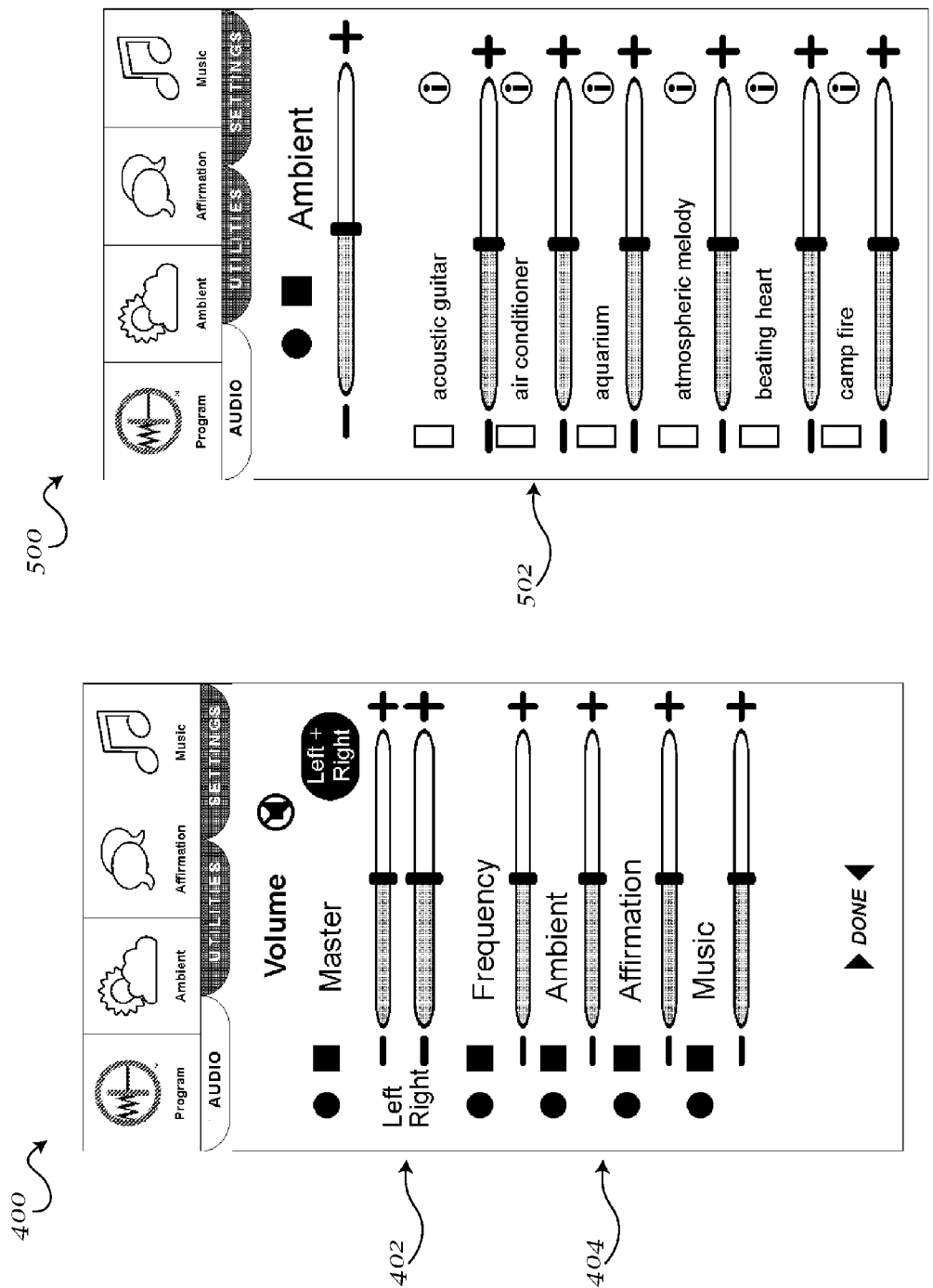

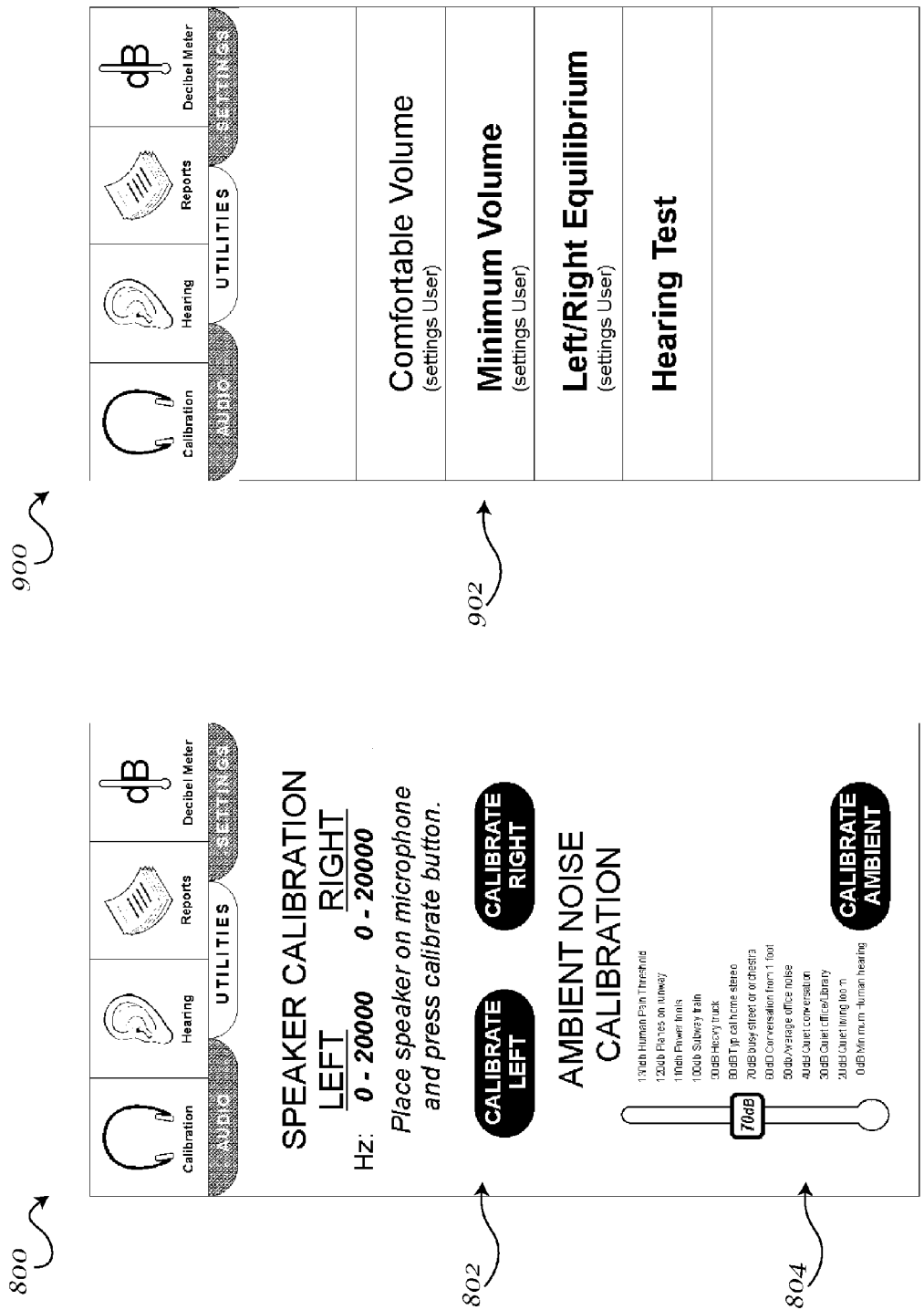

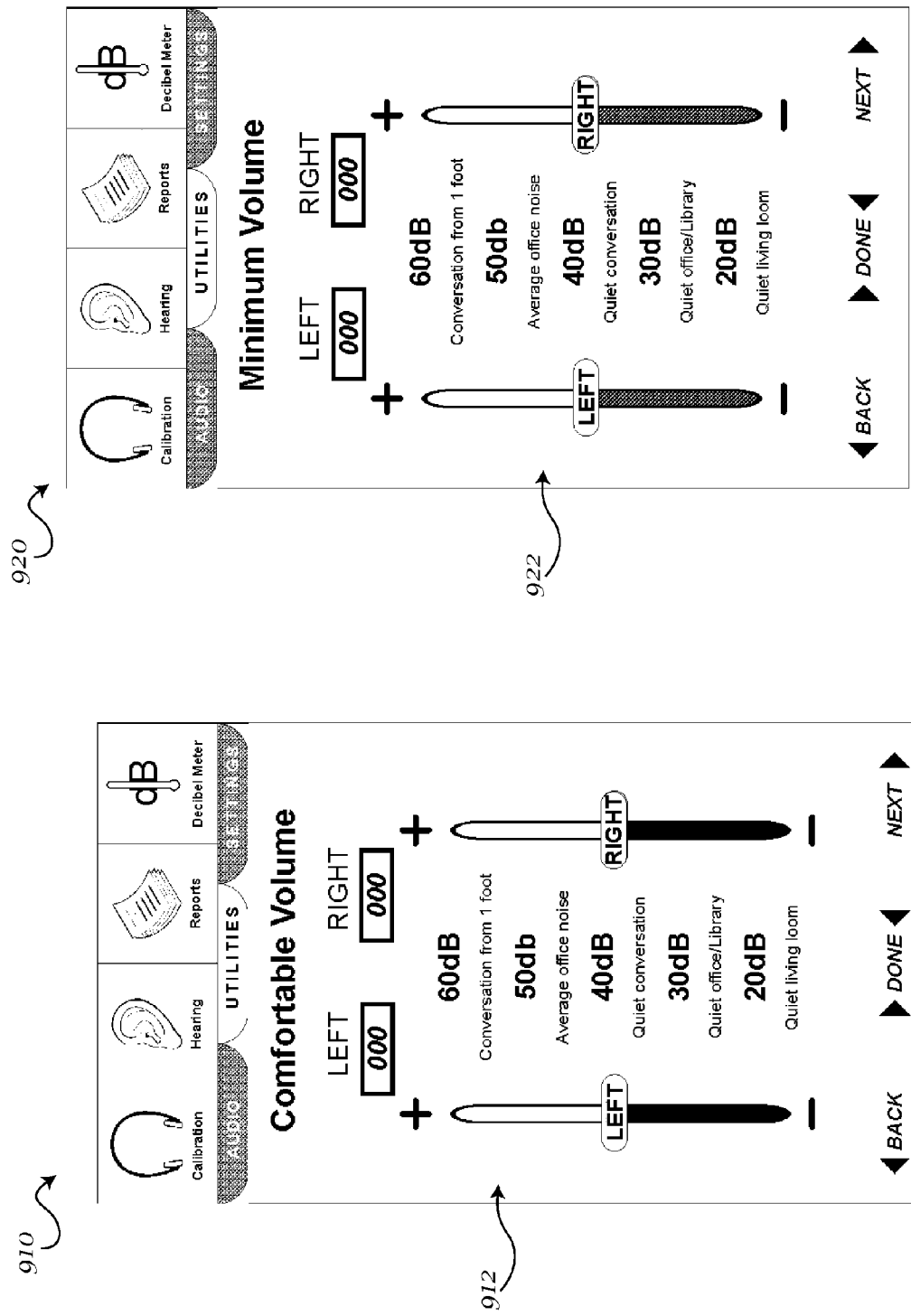

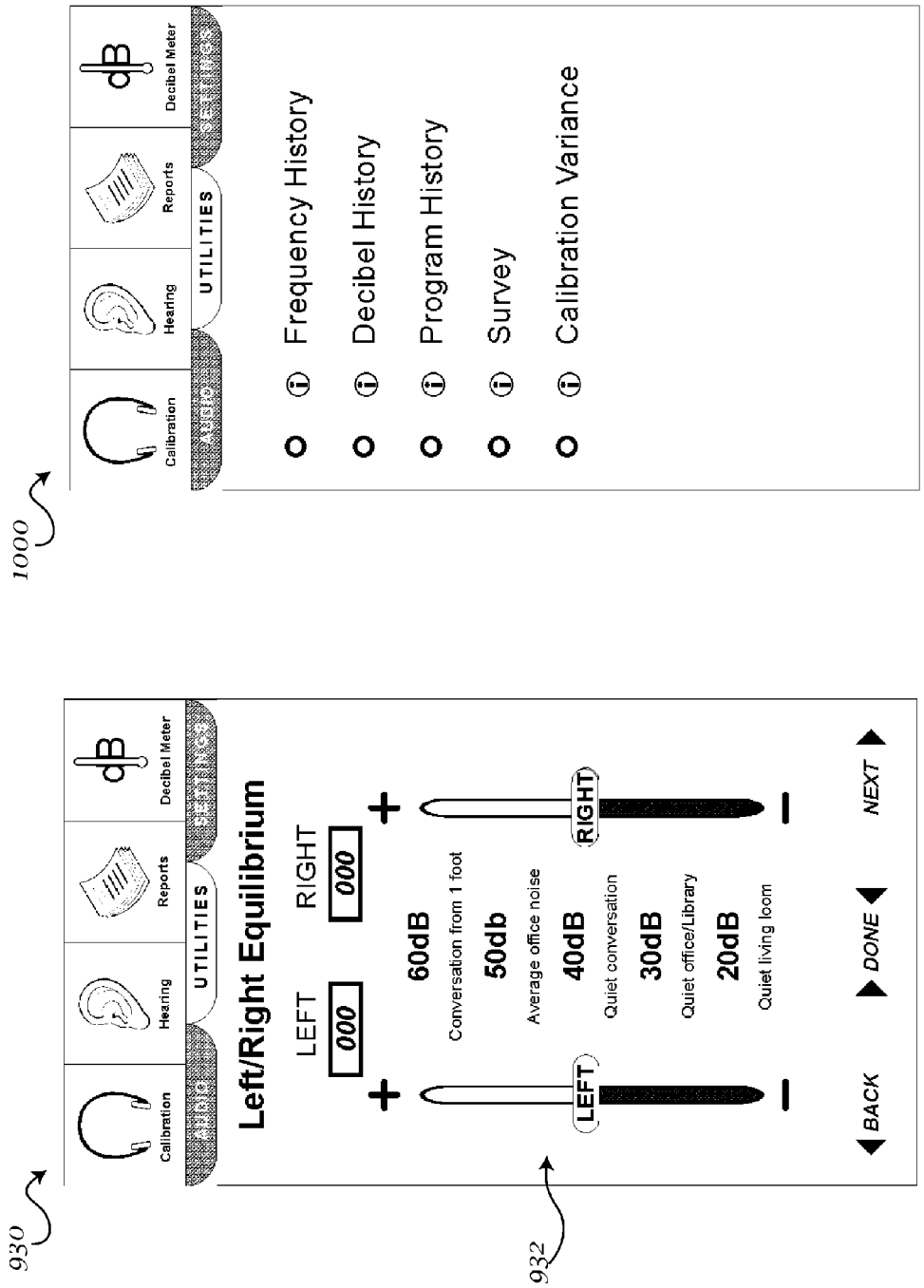

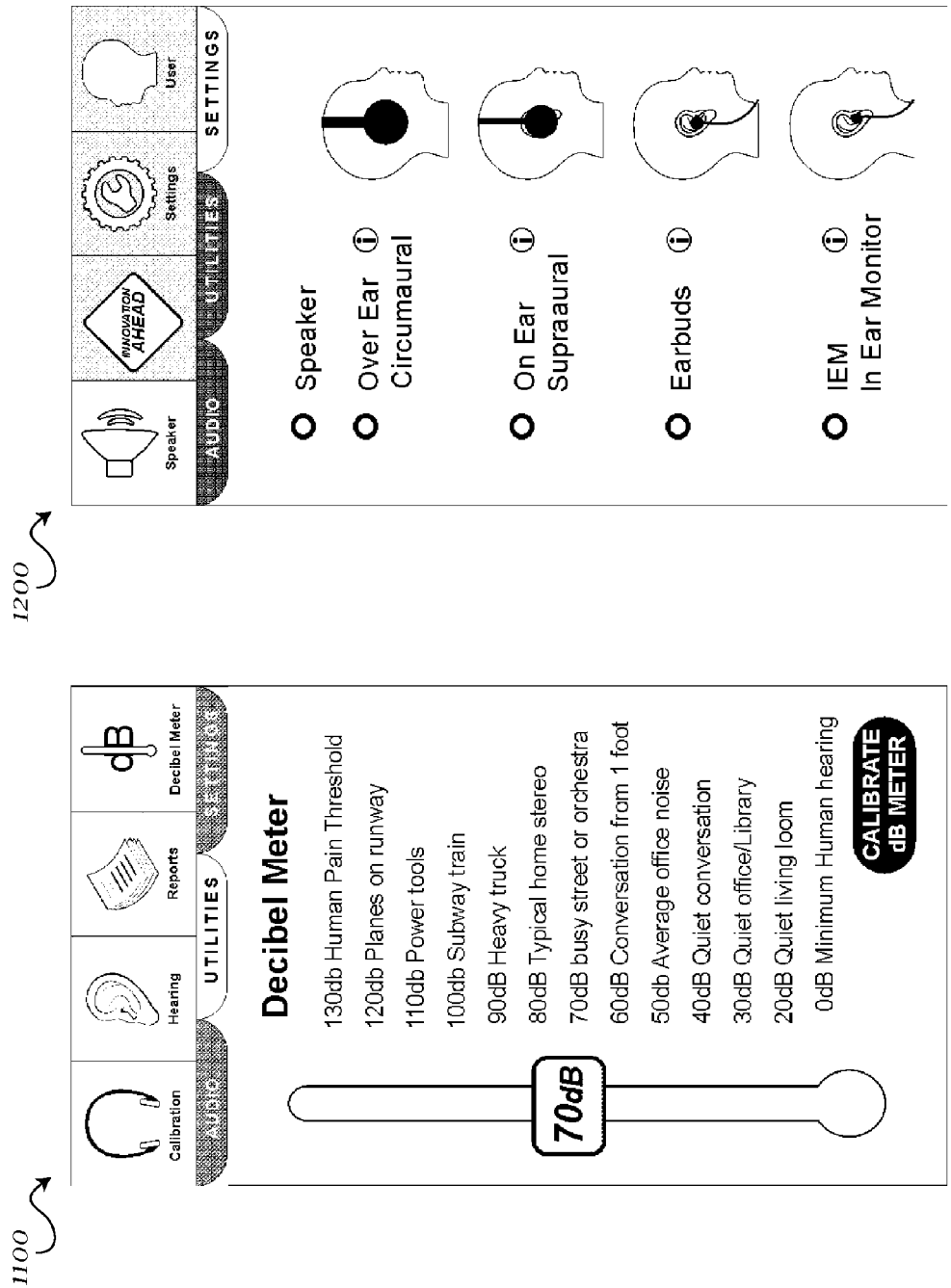

ary only. It should be understood that the described embodiments are not necessarily to be construed as preferred or advantageous over other embodiments. Moreover, the terms

METHOD, SYSTEM AND APPARATUS FOR INTEGRATED DYNAMIC NEURAL STIMULATION

CROSS-REFERENCE TO RELATED APPLICATIONS

This application claims priority to U.S. Provisional Application 61/600,354, filed Feb. 17, 2012 and entitled METHOD, SYSTEM AND APPARATUS FOR INTEGRATED DYNAMIC NEURAL STIMULATION, the entire contents of which are hereby incorporated by reference.

BACKGROUND

The use and function of audio playback devices are known. These devices can allow for the playback of audio data stored on a memory device using integrated speakers, connected speakers or headphones. However, such devices typically do not offer the opportunity to manipulate or calibrate the outputted audio data to the user beyond very limited adjustments.

Additionally, a variety of medical conditions exist related to hearing, sound, and headaches, amongst others, that can cause discomfort or other negative effects on a person. Treatment methodologies vary significantly, but tend to be too expensive or complicated for a typical person.

SUMMARY

According to at least one exemplary embodiment, a method for integrated dynamic neural stimulation is disclosed. The method can include selecting a tone for playback, adjusting the characteristics of the tone, selecting program options for modifying the playback of the tone, selecting an accompaniment to the tone, generating an audio program by combining the tone and the accompaniment according to the selected program options, and playing the audio program via an audio output device having at least a right channel and a left channel.

BRIEF DESCRIPTION OF THE DRAWINGS

Advantages of embodiments of the present invention will be apparent from the following detailed description of the exemplary embodiments. The following detailed description should be considered in conjunction with the accompanying figures in which:

FIG. 1a is a diagram of an exemplary computing device;

FIG. 1b shows an exemplary embodiment of a program customization interface;

FIG. 2a shows an exemplary embodiment of a frequency selection interface;

FIG. 2b shows an exemplary embodiment of a tone adjustment interface;

FIG. 4 shows an exemplary embodiment of a volume mixer interface;

FIG. 5 shows an exemplary embodiment of an ambient sounds interface;

FIG. 8 shows an exemplary embodiment of a calibration interface;

FIG. 9a shows an exemplary embodiment of a volume selection interface;

FIG. 9b shows an exemplary embodiment of a volume level interface;

FIG. 9c shows an exemplary embodiment of a minimum volume interface;

FIG. 9d shows an exemplary embodiment of a volume equilibrium interface;

FIG. 10 shows an exemplary embodiment of a reports interface;

FIG. 11 shows an exemplary embodiment of a decibel meter interface;

FIG. 12 shows an exemplary embodiment of a speaker selection interface.

DETAILED DESCRIPTION

Figures 2C, 3:
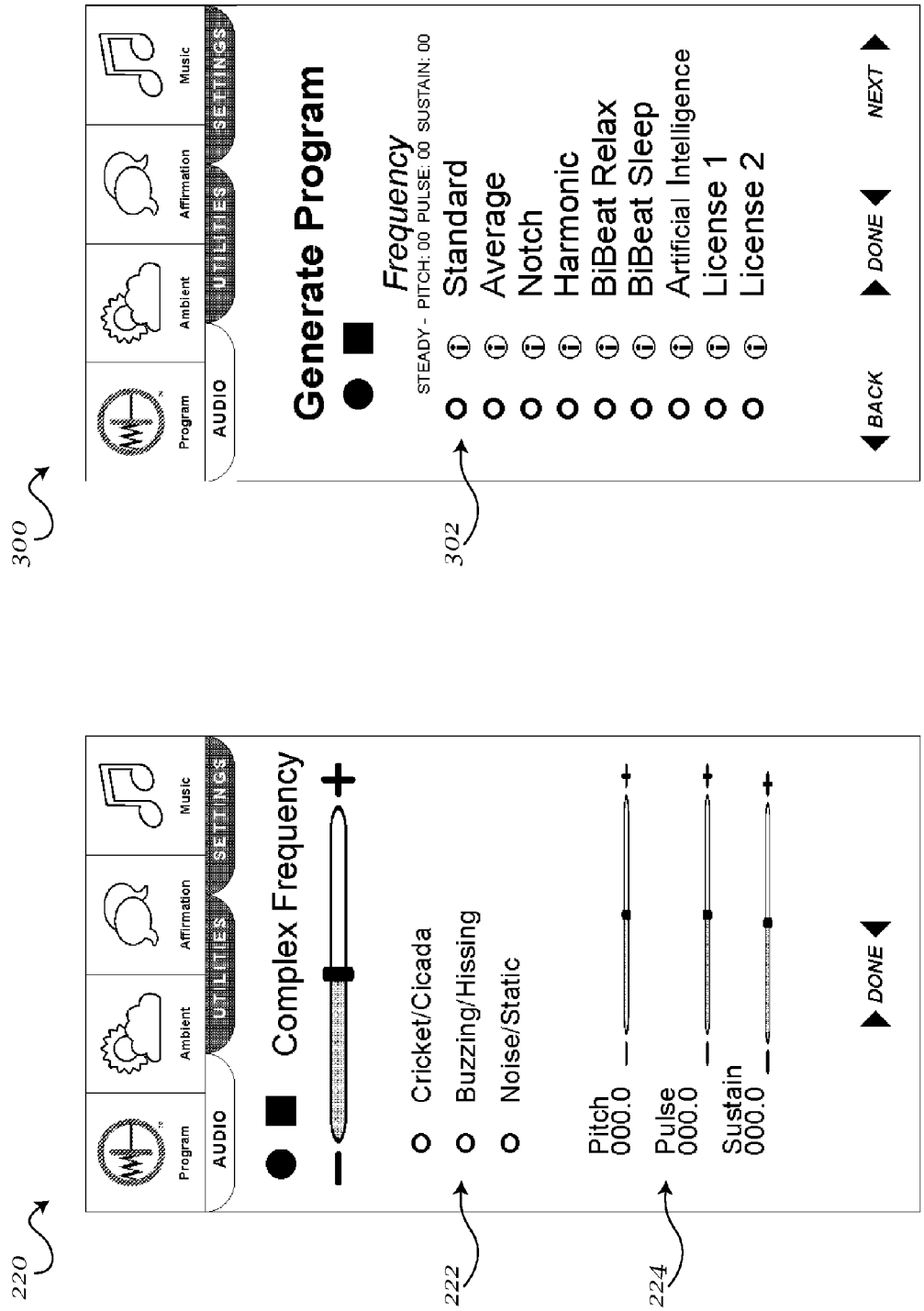
FIG. 2c shows an exemplary embodiment of a complex tone interface.
FIG. 3 shows an exemplary embodiment of a program generation interface.

Aspects of the present invention are disclosed in the following description and related figures directed to specific embodiments of the invention. Those skilled in the art will recognize that alternate embodiments may be devised without departing from the spirit or the scope of the claims. Additionally, well-known elements of exemplary embodiments of the invention will not be described in detail or will be omitted so as not to obscure the relevant details of the invention.

As used herein, the word "exemplary" means "serving as an example, instance or illustration." The embodiments described herein are not limiting, but rather are exemplary only. It should be understood that the described embodiments are not necessarily to be construed as preferred or advantageous over other embodiments. Moreover, the terms "embodiments of the invention", "embodiments" or "invention" do not require that all embodiments of the invention include the discussed feature, advantage, or mode of operation.

Further, many of the embodiments described herein are described in terms of sequences of actions to be performed by, for example, elements of a computing device. It should be recognized by those skilled in the art that the various sequence of actions described herein can be performed by specific circuits (e.g., application specific integrated circuits (ASICs)) and/or by program instructions executed by at least one processor. Additionally, the sequence of actions described herein can be embodied entirely within any form of computer-readable storage medium such that execution of the sequence of actions enables the processor to perform the functionality described herein. Thus, the various aspects of the present invention may be embodied in a number of different forms, all of which have been contemplated to be within the scope of the claimed subject matter. In addition, for each of the embodiments described herein, the corresponding form of any such embodiments may be described herein as, for example, "a computer configured to" perform the described action.

Generally referring to FIGS. 1-12, methods, systems and apparatuses for generating, manipulating and providing audio data may be described. The methods, systems and apparatus may be utilized to treat any of a variety of hearing conditions, for example, but not limited to tinnitus, treatment of other conditions, such as, but not limited to migraine headaches, insomnia, hypertension, concentration, relaxation, affirmation, or may simply be used for leisure. The method, system and apparatus can be implemented on any desired platform.

The software 10 may be utilized to house audio programs that can be manually and automatically calibrated for a user. There may be any number of desired values that can be adjusted by a user or by the software in order to provide for a desired audio output. Further, the software can be utilized to adjust an audio program over time to coordinate with a user's location, user's varying level of ambient noise, or changes in a user's symptoms or desired use.

As shown in FIG. 1a, the software 10 can be implemented on any type of computing device 20 that may be utilized to display data and provide an audio output, for example a smart phone, digital storage device, digital music player, computer and associated display, console and associated display and the like. The device 20 can include a non-transitory computer-readable medium 22 on which the software 10 can be stored, a processor 24 for executing the software 10, as well as a memory 26. The device 20 can include a display 28, which may be a touchscreen. The device 20 can have a graphical user interface that allows a user to view and manipulate data, for example via display 28 or with a peripheral device 30 such as a keyboard or mouse. For example, the device 20 can be a smartphone and different audio programs may be made, adjusted or otherwise utilized in a software application. The device can further include a sound input device 32, such as a microphone, and a sound output device 34, such as headphones, which may have at least a left and right channel.

The device 20 and software 10 can be utilized by a user to accomplish a variety of tasks. The software 10 may be generated and displayed in any manner and the figures shown herein should be viewed as demonstrative or exemplary. In one embodiment, the device 20 and its associated software 10 can be utilized to manipulate audio data to a user's desires or to treat a user's symptoms. The software 10 can provide for the adjustment of audio data in any of a multitude of fashions and can allow a user or treatment specialist to adjust audio data in order to treat a condition, for example. The software 10 may further allow for a user to select a generated, predesigned or pre-made audio program to play via the device. The program can be generated and adjusted by the software 10 in any of a variety of manners, as will be shown in the following exemplary embodiments. Additionally, program data, such as time, length or duration, output levels, balance and the like may be adjusted via the software. Further, accompaniments to a desired program, such as ambient sounds or music may be selected and any desired characteristics thereof may be edited or adjusted via the software. The software 10 can then add, subtract, or otherwise integrate the generated audio program with the accompaniment. Further, controls, such as volume controls and playback controls, may be shown or provided on the device 20 or by the software 10. The software may also be utilized to control any audio data or on board media housed on the device.

In a further exemplary embodiment, a program of audio data may be selected, created or customized. A program can be such that audio data, such as binaural tones that can be utilized in therapy, are provided at an appropriate level for a particular user. The audio data can be adjusted so as to provide a user with a tone that treats tinnitus through sound wave cancellation. Additionally, the tone may be adjusted by a user depending on variations to their symptoms, variations on ambient noise or any other appropriate or desired situation. For example, for a user who suffers from tinnitus, they may hear a constant tone in one or both ears. Thus a program of audio data that generates a corresponding tone to that caused by a user's tinnitus can cancel the undesired tone or otherwise alleviate the symptoms. Further, the playing of a tone that is exactly similar or very similar to a tone heard by tinnitus sufferers can be used as negative reinforcement insofar as the user's brain may choose to ignore the sound, to the benefit of the user. Further, positive reinforcement, such as mixing the sounds in a program with music or other desired ambient sounds, can distract a user from the tones and does not adversely affect their use in treating the symptoms.

As above, the audio data utilized in a program may be such that they treat symptoms of tinnitus, or any other condition. Due to the nature of such conditions, the symptoms may vary throughout the day depending on any of a variety of factors and the symptoms may be different in the left and right ears of a person suffering from such a condition. Thus, the ability to vary the output of audio data and adjust the settings at any desired time can be desired.

For example, the frequency (in hertz) of audio data can be adjusted, as well as the volume (in decibels). Other qualities of the sound that may be relevant to symptoms or situations, such as attack, decay, sustain and/or release, may be adjusted as desired. Further, the tone or sounds generated may be faded over a duration of time. This can allow user to attempt to phase out symptoms, such as tinnitus symptoms, or simply allow them to adjust the program to a desired level. For example, it may be desirable to fade a tone's volume over time in order to increase the effectiveness of audio therapy and eliminate risks of rebounding. Tones may also be completely removed or replaced with other audio data, for example ambient noise or music, at any desired time, manually or automatically. A length of a program may be selected or varied, and other sounds, such as ambient noises or music, may be added to a program and played in conjunction with the audio data. A program may thus be created, loaded, saved or otherwise edited using such an interface.

The software 10 can include a plurality of interface screens to allow the user to customize the outputted audio data as desired. Additionally, for navigating through the various features of the software, a navigation bar 102 can be presented, as shown in FIG. 1b. The navigation bar can allow the user to choose between a plurality of main categories 104, for example "Audio," "Utilities," and "Settings." Each category can have a plurality of subcategories 106, which can allow the user to access the particular features of the software. In the exemplary embodiment, the "Audio" category can include subcategories relating to customizing the outputted data, including audio data programs, ambient sounds, affirmations, and music.

A user can customize an audio data program via a program customization interface 100, as shown in exemplary FIG. 1b. The interface 100 can present the user with a plurality of options for customizing the audio data program that is output by the software 10. These options can include frequency 110, program generation 112, program timing 114, and volume mixer 116. By selecting one or more of these options, the user can tailor the outputted audio program as desired. Interface 100 can also include a decibel meter 108, which is described in further detail below.

Selecting the frequency option 110 can present the user with a frequency selection interface 200, as shown in exemplary FIG. 2a. The frequency selection interface screen can provide options for the generation of the tones or sounds used in a program. The tones or sounds in a program can be varied so that they can play steadily or to have a complex nature, or to be played in any other desired manner. For example, the user can select ringing tone option 202 to play a steady tone, or complex tone option 204 to play a tone having a complex nature.

Selecting ringing tone option 202 can present the user with tone adjustment interface 210, shown in FIG. 2b. Tone adjustment interface 210 can allow the user to adjust the characteristics of a steady tone that can be used in a program. Frequency adjustment controls 212 can allow for adjustment of the frequency, for example from a level of about zero Hz to a level of about 15,000 Hz or more. As for all controls, a slide bar, radio button or any other known control or manner of manipulating data may be utilized. Furthermore, the user may also adjust the pitch and pulse of the tone, for example via a pitch control 214 and pulse control 216.

In some exemplary embodiments, further adjustments for the frequency of the sounds in a program may be provided. For example, instead of a single frequency, a user may select a range of frequencies that can play in a program which could match a range of frequencies that are generated by tinnitus that is affecting the user. For example, if the user suffers from a fluctuating tone, a corresponding fluctuating tone may be played as part of a program.

In some exemplary embodiments, a user may desire to have the same sound played in both ears. In other exemplary embodiments, for example in the case of a tinnitus sufferer who has a first tone or volume in one ear and a second tone or volume in their other ear, they may desire to have a program play different tones, for example, out of each speaker on a pair of headphones. Thus, the software 10 can allow the a user to tailor sounds for each ear, for example by selecting a different frequencies control 218. The user can then utilize pitch control 214 and pulse control 216 to adjust the characteristics of the tone for each ear.

If a user desires to play a complex tone, the user can select complex tone option 204. The software 20 can then display complex tone interface 220. The complex tone interface 220 can include additional details to a program may be shown. A list of complex sounds 222 can allow the user to select complex sounds that may be worked into a program. Such complex sounds can include, for example, cicada noises, cricket sounds, buzzing/hissing sounds, noise/static sounds or any other desired sound. Parameter controls 224 can allow for adjustment of the complex sounds for any of a variety of parameters. These parameters can include, but are not limited to pitch, pulse, sustenance and the like.

Once the user selects a desired type of tone and the options for that tone, the user can select the program generation option 112 to select the type of program to be generated. As shown in FIG. 3, a program generation interface 300 can present the user with a plurality of options 302 for the program type. The program type options can affect the way the generated program is combined with its accompaniments, which are described further below. For example, the program type options can include standard, average, notch, harmonic, binaural beats that may be tailored for relaxation, sleep, or other purposes, artificial intelligence, or licensed options. For example, the notch option can subtract the generated tone of the tinnitus frequency from an accompaniment.

The user can adjust the length of time that a program is playing by selecting the program timing option 114. Selecting this option can provide the user with a plurality of program duration options. These can include, but are not limited to, a timer, a sleep timer or automatic shut-off and a wake timer or automatic start. Any other known programming capabilities for starting or stopping a program can be utilized as well. These can further include the ability to fade the generated tones or sounds over a duration of time.

To adjust the volume of the outputted audio data, the user can select volume mixer option 116. This can present the user with the volume mixer interface 400, shown in FIG. 4. The mixer interface 400 can include master volume controls 402. In some exemplary embodiments, a user may desire to have the outputted audio played at the same volume in both ears. In other exemplary embodiments, for example in the case of a tinnitus sufferer who has a first volume in one ear and a second volume in their other ear, they may desire to play the outputted audio at a different volume out of each speaker on a pair of headphones. Thus, master volume controls 402 may be configured so as to output the same volume in both the left and right ears, or to output a different volume level for each ear, as desired. The sound levels that can be utilized with a program may vary from about 20 dB or less to about 60 dB or more. The mixer interface 400 can further include mixer controls 404, which can allow the user to control the relative volumes of each portion of the outputted audio, for example, the generated tone, and the accompaniments such as ambient sounds, affirmations, music, and so forth.

In some exemplary embodiments, the user can select accompaniments to the generated tone to be played concurrently with the generated tone. These accompaniments can include, but are not limited to, ambient sounds, affirmations, and music. The accompaniment category may be selected via navigation bar 102, and the particular accompaniment can then be selected via a corresponding interface.

FIG. 5 shows an exemplary ambient sounds interface 500. Interface 500 can show a list 502 of potential options of ambient noise or sounds to be included with a program. Such ambient sounds include, but are not limited to, acoustic guitar, air conditioner, aquarium, atmospheric melody, beating heart, and/or camp fire. Such ambient sounds, as well as any others, can be considered soothing or relaxing and therefore may be desired by a user to be included with a program. The ambient sounds interface 500 can allow the user to select one or more of the listed ambient sounds, as well as to adjust the volume of all or each ambient sound.

Figures 6, 7:
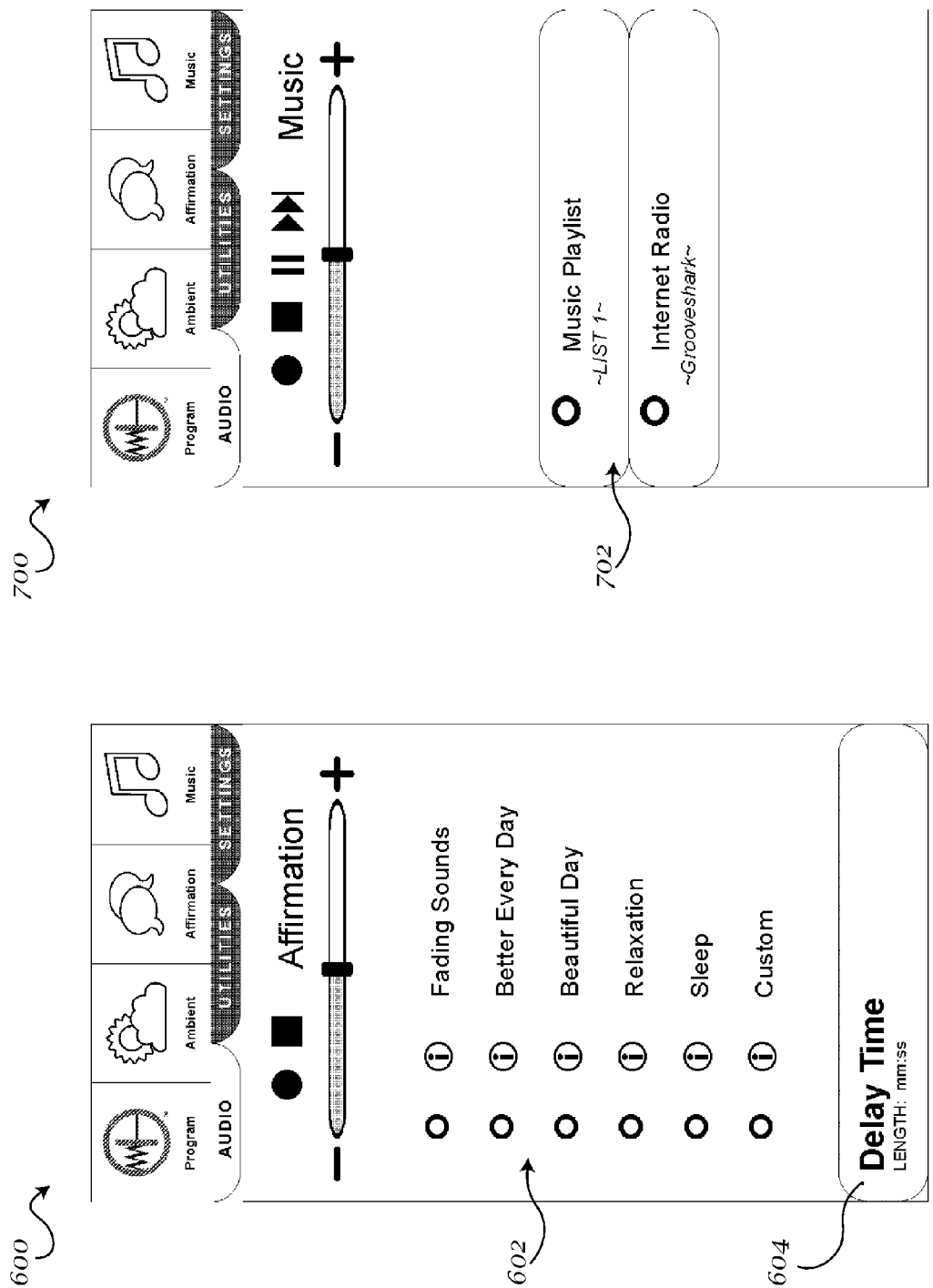
FIG. 6 shows an exemplary embodiment of an affirmations interface.
FIG. 7 shows an exemplary embodiment of a music interface.

FIG. 6 shows an exemplary affirmations interface 600. Interface 600 can show a list 602 of potential affirmations to be included with a program. The affirmations can provide positive reinforcement or soothing thoughts to a user. Such ambient sounds can include, but are not limited to, fading sounds, better every day, beautiful day, sleep, or custom affirmations. For example, the affirmations can tell the user "today your tinnitus is gone," "today is a beautiful day," "it's getting better every day," or any other desired statement. The affirmations interface 600 can allow the user to select an affirmation for playback, as well as to adjust the volume of the affirmation. The affirmations interface can also provide a delay timer 604, which can allow the user to enter a delay time before beginning playback of the affirmations. This can allow, for example, the user to fall asleep and for the affirmations to be played while the user is asleep.

FIG. 7 shows an exemplary music interface 700. Interface 700 can show a list 702 of potential options of music to be included with a program. These can include, but are not limited to, music from the music library present on the device 20, for example preprogrammed or generated playlists, music played by internet radio stations, or music from any other desired source. The music interface 700 can allow the user to select a music source for playback, as well as to adjust the volume of the music.

In some exemplary embodiments, the software 10 can allow for calibration of the speakers. An exemplary calibration interface 800, as shown in FIG. 8, may be accessed via the utilities category on navigation bar 102. The calibration interface can present the user with the option to calibrate the left and right speakers 802, and to calibrate for ambient noise 804. This can allow for compensation for the variance between the left and right speakers, as well as compensation for ambient noise. Calibration of the left and right speakers may be performed by placing both speakers, in succession, up to the microphone of the device 20. The software 10 can then play a tone through the speaker which can then be received by the microphone. The software 10 can then analyze the difference, for example in decibels, between the emitted and the received sound to calibrate the speaker. The software 10 can then analyze the difference, for example in decibels, between the received sound from the left and the right speaker to calibrate the speakers with respect to each other. Calibration of ambient noise may be performed by the software, by determining the ambient noise level received through the microphone of the device 20. Calibration allows the software to account for tone and volume variances in the speakers, and can reduce the risk hearing loss by preventing excessive volume levels that may be potentially damaging.

In some exemplary embodiments, the software 10 can allow for the selection of output volume levels in both speakers. An exemplary volume selection interface 900 is shown in FIG. 9a. The volume selection interface can present the user a list of options 902 to select a comfortable volume level, a minimum volume level, an equilibrium between the left and right speakers, and to perform a hearing test. As shown in FIG. 9b, a comfortable volume level interface 910 can allow the user to select a comfortable volume level, for each ear, via volume controls 912. This level may be chosen by a user or, in the event that a user has some hearing loss or sensitive hearing, the level can be adjusted manually by the user or automatically by the software 10, for example, based on the results of a hearing test. As shown in FIG. 9c, a minimum volume level interface 920 can allow the user to select the minimum volume level that the user can hear, in each ear, via volume controls 922. This level may be chosen by a user or, in the event that a user has some hearing loss or sensitive hearing, the level can be adjusted manually by the user or automatically by the software, for example, based on the results of a hearing test. As shown in FIG. 9d, a left/right equilibrium interface 930 can allow a user to balance the volume of the program in their left and right ears, as desired, via volume controls 932. Further, the device 20 and associated software 10 can include a hearing test. During the hearing test, the software can play a series of tones and sounds at various volumes to the users. The hearing test can be used in conjunction with the above interfaces 910, 920, 930. The hearing test can allow the user to easily set their comfortable hearing levels, minimum hearing levels, and left/right equilibrium based on the tones played by the software.

FIG. 10 shows an exemplary interface for reports 1000. As the software 10 can track use of various programs, settings, usage and any other details relevant to the software, reports may be generated that can provide a user or medical personnel with feedback. For example if a user has progressively lowered the volume of a tone on a program, it may provide a positive diagnosis that the system is helping the user. Additionally, if tone frequency is varied or changed, it can allow a user to make other appropriate changes or give them a deeper understanding of their symptoms. Any desired conditions or factors related to a program may be stored and displayed in any desired manner, for example as numerical data, graphed data or any other known form and a software application can calculate and display them in any desired fashion.

Exemplary FIG. 11 shows a decibel meter 1100. The decibel meter can be set by a user to the level of ambient noise that is occurring around them. For example a person who is at home in their living room may set a very low ambient noise level whereas a person at a construction site may have a very high ambient noise level. In some further exemplary embodiments, when a program is running a microphone may also be utilized to determine ambient sound levels and the application can adjust a program may be adjusted automatically to compensate for varying levels of ambient noise. Similarly, a microphone may be used at any time to determine the level of ambient sound and make any automatic or desired adjustments based on the incoming audio data.

Exemplary FIG. 12 shows a speaker type selection interface 1200. As the device 20 on which the software 10 is implemented can be any type of device, as described previously, a number of different speaker types may be utilized to play the audio data of a program. For example regular stereo or television speakers may be used, earbud-style headphones may be used, on-ear headphones may be used, over-the-ear headphones may be used, in ear monitors may be used, and any other type of speaker may be utilized. As each of these types of speakers can provide for differing sound quality or differing audio environments, for example allowing more ambient noise to be heard by the user, the user can therefore select the appropriate speaker type order to compensate for chosen speaker system. Further, as discussed above, the speakers can be calibrated so as to further tailor the audio playback and adjust for clarity or any other desired quality. Speaker calibration can be performed by holding an appropriate speaker proximate to a microphone.

As the method, system and apparatus may utilize artificial intelligence, they can be considered learning and adaptive. Thus, while the reports can provide users with feedback, they can also be used to automatically adjust or tailor a program based on a user's needs and preferences. A program may automatically adjust at certain times of day when a user routinely moves from a more quiet location to a noisier location. Additionally, a program can automatically adjust a tone or frequency over time based on changing symptoms of a user and predicting future symptoms.

The foregoing description and accompanying figures illustrate the principles, preferred embodiments and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. A method for integrated dynamic neural stimulation, comprising:
   selecting a tone for playback;
   determining at least one second tone corresponding to at least one symptom of a medical condition of a user;
   adjusting the characteristics of the tone including generating a third tone that corresponds to the second tone to treat the at least one symptom of the user's medical condition through sound wave cancelation;
   selecting program options for modifying the playback of the tone;
   selecting an accompaniment to the tone;
   generating an audio program by combining the tone and the accompaniment according to the selected program options; and
   playing the audio program via an audio output device having at least a right channel and a left channel.

2. The method of claim 1, wherein the program options are selected from one of standard, average, notch, harmonic, binaural beats, and artificial intelligence.

3. The method of claim 1, wherein the characteristics of the tone comprise volume, frequency, pitch, pulse, sustenance, and complex sounds.

4. The method of claim 1, further comprising calibrating the audio output device.

5. The method of claim 4, wherein calibrating the audio output device further comprises one or more of calibrating the left and right channels, calibrating for ambient noise, adjusting left/right channel equilibrium, setting comfortable volume levels and setting minimum volume levels.

6. The method of claim 1, wherein the accompaniment is selected from one of ambient sounds, affirmations, and music.

7. The method of claim 1, wherein adjusting the characteristics of the tone further comprises:
   adjusting characteristics for playback in the left channel; and
   adjusting characteristics for playback in the right channel.

8. The method of claim 7, wherein the characteristics of the tone comprise volume, frequency, pitch, pulse, and sustenance.

9. The method of claim 8, wherein the characteristics of the tone played in the right channel differ from the characteristics of the tone played in the left channel.

10. A system for integrated dynamic neural stimulation, comprising:
    a computing device, the computing device including a non-transitory storage medium, a processor, a memory, and an audio output device having at least a right channel and a left channel;
    an audio software, the audio software being adapted to allow a user to select a program option from a list of program options and to generate an audio program by combining a tone and an accompaniment according to the selected program options, and to play the audio program via the audio output device;
    selecting a tone for playback;
    determining at least one second tone corresponding to a user's tinnitus;
    adjusting the characteristics of the tone including generating a third tone that corresponds to the second tone to treat the user's tinnitus through sound wave cancelation;
    selecting program options for modifying the playback of the tone;
    selecting an accompaniment to the tone;
    generating an audio program by combining the tone and the accompaniment according to the selected program options; and
    playing the audio program via an audio output device having at least a right channel and a left channel.

11. The system of claim 10, wherein the program options comprise standard, average, notch, harmonic, binaural beats, and artificial intelligence.

12. The system of claim 10, wherein the audio software is further adapted to allow a user to select a tone and to adjust the characteristics of the tone.

13. The system of claim 12, wherein the characteristics of the tone comprise volume, frequency, pitch, pulse, sustenance, and complex sounds.

14. The system of claim 10, wherein the accompaniment comprises ambient sounds, affirmations, and music.

15. The system of claim 10, wherein the audio software is further adapted to allow a user to separately adjust the characteristics of the tone for the left channel and the characteristics of the tone for the right channel.

16. The system of claim 15, wherein the characteristics of the tone comprise volume, frequency, pitch, pulse, and sustenance.

17. The system of claim 16, wherein the characteristics of the tone played in the right channel differ from the characteristics of the tone played in the left channel.

18. The system of claim 10, wherein the software is further adapted to allow a user to calibrate the left and right channels, calibrate for ambient noise, adjust left/right channel equilibrium, set comfortable volume levels and set minimum volume levels.

19. The system of claim 10, wherein the computing device further comprises an audio input device.

20. The system of claim 19, wherein the audio software is further adapted to allow a user to calibrate the audio output device by emitting sound via the audio output device while placing the audio output device proximate the audio input device.

* * * * *